United States Patent [19]

Onozuka et al.

[11] 4,010,141
[45] Mar. 1, 1977

[54] ANTI-FOULING COMPOSITION FOR USE IN WATER COMPRISING A POLYMER AND AN ORGANO TIN COMPOUND

[75] Inventors: Mitsuo Onozuka; Yasuo Hayashi; Yoshiaki Adachi, all of Iwaki, Japan

[73] Assignee: Kureha Kagaku Kogyo Kabushiki Kaisha, Tokyo, Japan

[22] Filed: Jan. 10, 1975

[21] Appl. No.: 540,202

Related U.S. Application Data

[63] Continuation-in-part of Ser. No. 248,270, April 17, 1972, Pat. No. 3,861,949.

[30] Foreign Application Priority Data

Apr. 27, 1971 Japan .............................. 46-27158
Nov. 1, 1971 Japan .............................. 46-86263
Dec. 27, 1971 Japan .............................. 47-105482

[52] U.S. Cl. .......................... 260/45.75 K; 424/78; 424/288; 106/15 R
[51] Int. Cl.² ......................................... C08K 5/57
[58] Field of Search ................. 260/47.75 K, 429.7; 424/288, 78; 106/15 AF

[56] References Cited

UNITED STATES PATENTS

| | | | |
|---|---|---|---|
| 2,957,785 | 10/1960 | Leatherland | 106/15 AF |
| 3,198,819 | 8/1965 | Gloskey | 260/429.7 |
| 3,684,752 | 8/1972 | Goto et al. | 424/288 |

*Primary Examiner*—V. D. Turner
*Attorney, Agent, or Firm*—Sughrue, Rothwell, Mion, Zinn & Macpeak

[57] ABSTRACT

In an article to be used in or under water and in constant contact with the water, at least the surface of the article is composed of an anti-fouling composition which comprises a polymer and an organo tin compound of the formula:

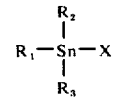

wherein $R_1$ is n-dodecyl and $R_2$ and $R_3$ are methyl. X is defined in the specification.

3 Claims, No Drawings

ANTI-FOULING COMPOSITION FOR USE IN WATER COMPRISING A POLYMER AND AN ORGANO TIN COMPOUND

CROSS-REFERENCE TO RELATED APPLICATION

This application is a continuation-in-part of U.S. application Ser. No. 248,270, Onozuka et al, filed Apr. 17, 1972, now U.S. Pat. No. 3,861,949.

BACKGROUND OF THE INVENTION

1. Field of the Invention

This invention relates to a process for attaining anti-fouling of a constantly water-contacting surface of an article against deposition of water micro-organisms by the use of organo-tin compounds. It relates also to an article capable of providing such anti-fouling characteristic.

2. Description of the Prior Art

As the articles of the above kind, fishing and fish-cultivating nets, floats, boat hulls, fishery tools, ropes and the like can be mentioned.

When water micro-organisms such as barnacle, serpula, polyzoan, mussel, ascidian, laver, green laver and/or the like are attached onto the surface of a water-immersed article and grow thereover, the mechanical strength as well as the durable life of the article may be substantially reduced, as is very well known. In addition, especially in the case of fishing nets, the fluid resistance for the in- or out-flowing water through the meshes of the net becomes larger and larger, whereby in the case of fish cultivation in a limited area of the sea, for instance, in an area surrounded by such a net, the fishes under cultivation are adversely affected by a poor supply of oxygen dissolved in the water. In the case of a fishing net, the increases flow resistance gives rise to substantially increased man power needs for the fishery.

In order to minimize these drawbacks, fishing nets and the like articles floating on or immersed in the water must be frequently dried under daylight so as to kill the deposited and flourishing water micro-organisms, thus causing a large amount of additional man power to be consumed for this purpose and substantial mechanical damage of the net. These are sincere and grave troubles to the fishermen.

In the case of the culture of oysters and the like shell-fish, the deposit of water micro-organisms on the suspension ropes and floats of the culturing net will invite an increased weight thereof and the dipping depth of the suspended culture net will be correspondingly increased, which adversely affects the growth of the oysters. In the case of the fixed fishing net, the same cause as above referred to will reduce the yield of caught fish.

In order to avoid these conventional drawbacks, it has already been proposed to use inorganic anti-fouling agents such as cuprous oxide, mercury oxide or the like; organo-copper salts such as copper naphthenate, copper oleate or the like; an organo-tin compound such as bis-tributyl tin oxide, independently or in combination, so as to prevent deposition of water micro-organisms on the articles exposed to sea or river water. These substances are highly poisonous and known especially as effective agents of ship bottom anti-fouling paint. With use of these anti-fouling substances, various disadvantages have been encountered. As an example, the material of the articles to be protected has been found substantially deteriorated or damaged by the aggression of these agents per se, or of the modified substances therefrom in the presence of industrial fouling substances dissolved in the water. A further considerable disadvantage derived from the use of these conventional anti-fouling agents is such that these can be applied only through a coating technique. Especially, a uniform coating of these substances is highly difficult. In addition thereto, with the use of the developer as employed in the coating application of these anti-fouling agents, it has been frequently encountered that the developer is rather liable to dissolve into the water and the anti-fouling agent may frequently be scaled off from the applied article surface. On the other hand, when the developer is difficult to dissolve, the water-immersed article, such as fishing net and fishery rope, is liable to become stiffened and the anti-fouling agent is frequently scaled off within an unexpectedly short period.

SUMMARY OF THE INVENTION

It is the main object of the present invention to provide a process for preventing the fouling of articles exposed to water (hereafter often referred to as anti-fouling of water exposed articles) in an efficient and durable way, so as to suppress the deposition of water micro-organisms thereon, and an article having its entire surface effectively protected in this manner.

A subsidiary object is to provide a process and an article of the above kind, whereby no deterioration of the article is substantially invited.

A further subsidiary object is to provide a process and an article of the above kind, whereby substantially no poisonous effect is provided, not only upon the treating personnel, but also upon fishes living in the water.

For fulfillment of these objects, it is proposed by the present invention to use an organo-tin anti-fouling agent having a trialkyl tin radical, one of the three alkyl radicals coupled with the tin being an n-dodecyl radical. This kind of organo-tin anti-fouling agent has a substantially low solubility in water and thus dissolves in the water only sparingly. Therefore, the agent does not readily lose its initial concentration on the article's surface when it is applied thereto by coating or blending, as will become more clear as the description proceeds, whereby its effectiveness is guaranteed for an extended time period.

By the very presence of the n-dodecyl radical in the molecular structure of the anti-fouling agent, a proper mutual solubility is obtained with a synthetic resin material when the latter is used as the material of the article to be protected in the water, thereby providing convenience and advantages when the anti-fouling agent is used through blending, so as to provide an evenly comixed blend.

DETAILED DESCRIPTION OF THE INVENTION

The improved trialkyl tin compound used as the anti-fouling agent has a satisfactory thermal stability over conventional trialkyl tin compounds of lower alkyls, without fear of loss of effectiveness even through blending at an elevated temperature.

When the article is manufactured from such a blended material, it has been observed that the anti-fouling agent will bleed out from the interior towards the surface of the article, whereby the anti-fouling effect is supplemented with lapse of time and is maintained for a prolonged period.

The superior blending characteristics of the anti-fouling agent with a synthetic resin, or more specifically, the improved thermal stability, mutual solubility and bleedability, can be still further improved by proper selection of the anionic substituent radical of the anti-fouling, organo-tin trialkyl compound.

In place of blending the organo-tin trialkyl compound, a mixture of the compound with a synthetic resin may be dissolved or suspended in a solvent and the solution or suspension can be applied by coating.

The application of the organo-tin trialkyl compound proposed by the invention to a synthetic resin to protect the article made of the resin, through either blending or coating, does not deteriorate the stability of the resin and various other advantageous physical properties thereof.

As an example, when the anti-fouling agent consisting of dimethyl-n-dodecyl tin stearate having such molecular structure:

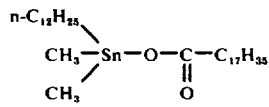

is blended with vinylidene chloride/vinyl chloride copolymer ("Krehalon") and the blended material is fabricated into fishing nets and like articles exposed to water, the following results have been obtained as tabulated in Table 1.

As ascertained by thin layer chromatography or IR-spectrum analysis, the anti-fouling agent consisting of the above stearate showed practically no deterioration during the blending process. This effect was ascertained by the said testing procedures by observing compound which had bled onto the article surface.

TABLE 1

| tested material | with no organic anti-fouling agent added | dimethyl-n-dodecyl tin stearate 1 PHR | 2 PHR |
|---|---|---|---|
| tensile strength (g/d) | 1.53 | 1.57 | 1.64 |

TABLE 1-continued

| tested material | with no organic anti-fouling agent added | dimethyl-n-dodecyl tin stearate 1 PHR | 2 PHR |
|---|---|---|---|
| elongation percentage (%) | 26.4 | 30.8 | 27.0 |
| knot strength (g/d) | 1.01 | 1.02 | 1.03 |
| thermo-stability 170° C/ 5 mins | yellow | yellow | yellow |
| 170° C/10 mins | " | " | " |
| 180° C/15 mins | " | " | " |

Remarks 1: compounding specification
"Krehalon" resin — 100 wt. parts
DEP (diethyl phthalate) — 2 PHR
alpha-MBE (dimethyl benzyl ether) — 3 "
barium stearate — 0.5 "
carbon black — 0.065 "

Remarks 2: spinning conditions
spinning unit (model: Beck-2)
nozzle, single orifice, 2 mm dia.
extrusion rate: 14 g/min; 1,000 denier. stretch: 3 times internal temp.: 170° C Remarks 3: Thermo-stability tests were carried out on a press and with use of the above compounding mixture, excluding the carbon black.

As for the toxicity, several tests were made with the use of, as an example, bis-(dimethyl-n-dodecyl tin)oxide and dimethyl-n-dodecyl tin stearate, which were compared with a conventional butyl tin compound. In these tests, the compound was coated on a polyethylene fishing net and a Krehalon resin net for carrying out tests on living fish. The results are shown in the following Table 2.

From these comparative tests, it will be seen that the toxicity of the above improved compounds upon living fish is lower than the comparative conventional anti-fouling agents.

As a further example, acute toxicity was tested by oral administration of the compound on mice. $LD_{50}$ was 0.88 g/kg and thus highly safe in comparison with $LD_{50}$ 0.2 g/kg of conventionally known bis-(tri-n-butyl tin)oxide.

TABLE 2

Toxicity Tests of Fishing Nets Coated with Organo-tin Anti-fouling Agents

| | Number | 1 | 2 | 3 | 4 |
|---|---|---|---|---|---|
| organo-tin anti-fouling agent | | bis-(dimethyl-n-dodecyl tin) oxide | dimethyl-n-dodecyl tin stearate | bis-(tri-n-butyl tin) oxide | tri-n-butyl tin stearate |
| containing percentage | | 5 wt. % | 5 wt. % | 5 wt. % | 5 wt. % |
| mixing rate of developer "Elbax-40" | | 5 wt. % | 5 wt. % | 5 wt. % | 5 wt. % |
| added quantity of solvent naphtha | | 90 wt. % | 90 wt. % | 90 wt. % | 90 wt. % |
| polyethylene fishing net | weight of fishing net, g | 7.84 | 8.00 | 7.98 | 7.87 |
| | total deposition quantity of anti-fouling agent and developer relative to the weight of net % | 4.3 | 3.7 | 3.4 | 3.7 |
| | weight of net, g | 7.87 | 7.69 | 7.89 | 7.87 |

TABLE 2-continued

| | | Toxicity Tests of Fishing Nets Coated with Organo-tin Anti-fouling Agents | | | |
|---|---|---|---|---|---|
| | Number | 1 | 2 | 3 | 4 |
| "krehalon" fishing net | total deposition quantity of anti-fouling agent and developer relative to the weight of net, % | 1.6 | 1.6 | 1.6 | 1.5 |
| time for complete mortality, hrs. | | 44 | no mortality (even after lapse of 480 hours) | 20 | 44 |

Remarks:
1. The area of net coated: 10 cm × 20 cm
2. "Elbax-40" consists of ethylene (60 wt. %)/vinyl acetate (40 wt.%) copolymer (melt index: 255)
3. The used vessel is a steel vat, enameled, 30 cm (dia.) × 30 cm (height)
4. 4.0 g, mean length: 6.0 cm were introduced in each of these vats. Then, these fish were left alone for 24 hours and then two fishing nets having the size given above and being coated with the anti-fouling agent on the polyethylene of the nets were introduced into each of the vats and the mortality observed for the necessary time period
5. Water temperature: 20° C, water quantity: 30 lit./vat.

Based upon the aforementioned objects and experimental results, the process features of the present invention reside in a method for the prevention of fouling of an article by deposition of water micro-organisms by application of a composition comprising an organo-tin compound of the general formula:

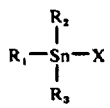

where $R_1$ is n-dodecyl and $R_2$ and $R_3$ are methyl, and X has the meaning set forth below, and a synthetic resin protecting at least the exposed surface of said article.

The invention relates further in such article as to be used in or on the water, at least the surface of said article beind composed of an anti-fouling composition comprising a polymer and an anti-foulingly effective substance comprising in turn an organo-tin compound as expressed by the following general formula:

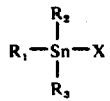

wherein $R_1$ stands for n-dodecyl and $R_2$ and $R_3$ stand for methyl; X stands for:
a. the group

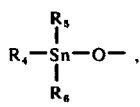

wherein $R_4$ is a $C_8$–$C_{12}$ higher alkyl group and $R_5$ and $R_6$ are $C_1$–$C_3$ lower alkyl groups, the total number of carbon atoms in $R_1$, $R_2$ and $R_3$ being less than 15. Most preferably, $R_1$ is n-dodecyl and $R_2$ and $R_3$ are methyl.
b. halogen;
c. alkoxyl;
d. thioalkoxyl;
e. an organic acid radical; or
f. a surfactant radical, exclusive of active hydrogen, ammonium or a metallic radical.

Examples of $R_4$ are n-octyl, 2-ethylhexyl, n-decyl and n-dodecyl.

Examples of $R_5$ and $R_6$, which may be the same or different from each other, are methyl, ethyl, n-propyl and i-propyl.

X, when halogen, is preferably chlorine, bromine or iodine.

In the case of X being an alkoxyl radical, it contains 3 to 24 carbon atoms. It may be an alcohol residue, illustrating mono-, di- or trivalency. It may be derived from an alcohol group consisting of a saturated or unsaturated, straight chain or branched aliphatic alcohol, a saturated or unsaturated cyclo-aliphatic alcohol or an aromatic alcohol such as: n-propyl alcohol; i-propyl alcohol; n-butyl alcohol; sec.-butyl alcohol; i-butyl alcohol, t-butyl alcohol; n-amyl alcohol; 1-amyl alcohol; 2-ethyl-1-butanol; neopentyl alcohol; diethylcarbinol; 2-pentanol; methyl isopropyl carbinol; t-amyl alcohol; n-hexyl alcohol; dimethyl isopropyl carbinol; n-heptyl alcohol; n-octyl alcohol; n-decyl alcohol; n-dodecyl alcohol; myristyl alcohol; hexadecanol; n-octadecanol; allyl alcohol; crotyl alcohol; methyl vinyl carbinol; allyl carbinol; methylpropenyl carbinol; 4-pentene-2-ol; 10-undecen-1-ol; propagyl alcohol; 2-butyne-1-ol; 2-pentyne-1-ol; 1,4-pentadiene-3-ol; ethyl-cello-solve; butyl-cello-solve; propylene glycol; ethylene glycol; 2-methyl-1,2-propanediol; trimethylene glycol; 2,4-pentanediol; hexamethyltrimethylene glycol; tetramethylene glycol; 1,4-hexanediol; 3-butene-1,2-diol; 2,5-dimethyl-3-hexene-2,5-diol; 2-butene-1,4-diol; glycerin; 1,2,3-pentanetriol; 2-methyl-1,2,3-propanetriol; 2-methyl-2,3,4-butanetriol; phenol; cresol; xylenol; propylphenol; butylphenol; catechol; resorcin; urushiol; guaiacol; eugenol; pyrogallol; cyclopropanol; cyclopropylethylene glycol; cyclobutyl methylcarbinol; cyclohexanol; 1,3-cyclohexanol; 1,3-cyclohexanediol; 1-cyclohexanol; benzyl alcohol; naphthol and the like.

X, when thioalkoxyl, contains 3 to 24 carbon atoms and may be selected from the following group of thioalcohols (mercaptans) giving a thioalcoholic radical of mono-, di-, or tri-valency, such as: n-propylmercaptan; i-propylmercaptan; n-butylmercaptan; i-butylmercaptan; t-butylmercaptan; n-amylmercaptan; i-amylmercaptan; n-hexylmercaptan; n-octylmercaptan; 2-ethylmercaptan; n-decylmercaptan; n-dodecylmercaptan; n-hexadecylmercaptan; neopentylmercaptan; allymercaptan; 3-N,N-diethylaminopropylmercaptan; 1,2-dithioglycerol; 2,2-dimercaptopropane; 1,1-dimercaptocyclohexane; thiophenol; o-mercaptobenzoate; o-chlorothiophenol; m-bromothiophenol; p-thiocresol; ethyl-beta-mercaptocinnamate; alpha-mercaptohtiophene; thioacetic acid; dithioacetic acid, beta-mercaptopropionic acid and the like.

The thioalcoholic radical may be derived from a straight chain or branched aliphatic thioalcohol or a saturated or unsaturated cycloaliphatic thioalcohols or aromatic thioalcohols.

X, when an organic acid radical, may preferably be derived from organic acids ($C_2$–$C_{24}$) of a mono-, di- or tribasic character; such as: acetic acid; propionic acid; butyric acid; valerianic acid; caproic acid; pelargonic acid; caprinic acid; n-undecylenic acid; myristic acid; palmitic acid; lauric acid; margarine acid; stearic acid; behenic acid; methacrylic acid; lignoceric acid; vinyl acetatic acid; tiglic acid; 4-pentenic acid; alpha-ethylcrotomic acid; 2-octenoic acid; 4-dodecenic acid; propiolic acid; 9-undecenoic acid; stearolic acid; 2,4-pentadienic acid; linileic acid; linolenic acid; malonic acid; succinic acid; adipic acid; dodecanedicarboxylic acid; maleic acid; fumaric acid; itaconic acid; benzoic acid; toluylic acid; phthalic acid; cinnenic acid; alpha-allylphenylacetic acid; alpha-benzylacrylic acid; alpha-naphtoic acid; naphthalene-1,2-dicarboxylic acid; naphthalic acid; cyclopropanecarboxylic acid; 1-cyclohexenecarboxylic acid; 1-phenylcyclohexane carboxylic acid and the like.

Therefore, it will be seen that the acid under consideration may be preferably selected from saturated and unsaturated aliphatic carboxylic acids; cycloaliphatic carboxylic acids and aromatic carboxylic acids.

The main skeleton of each of these alkoxy radicals, thioalkoxyl radicals and organic acid radicals may have a branch substituent such as a: halogen, alkoxyl-, amino-, thioalkoxyl-, carbonyl-, or carboxylic acid radical.

The surfactant providing a surfactant radical may have a functional radical comprising at least one active hydrogen, such as —$NH_2$; —NHR; —OH; —SH; —COOH or the like, and the active hydrogen may be substituted for or replaced by a metallic or ammonium atom. The surfactant may have at least one such radical(s) in its molecule. This surfactant may be a commercially available anti-static agent adapted for blending.

Certain of these may be:

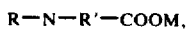

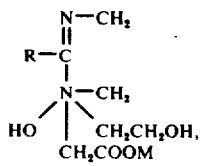

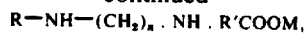

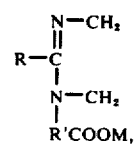

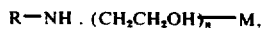

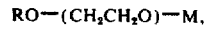

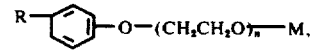

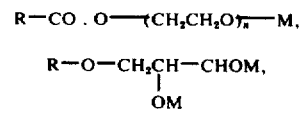

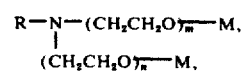

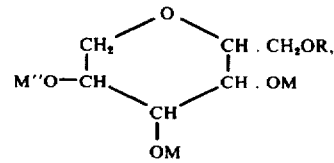

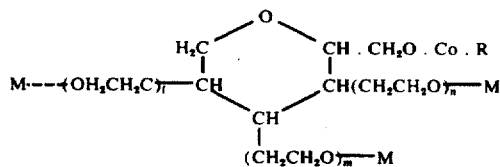

The synthetic resin to be admixed or blended with the organo-tin compound employable in this invention may be: a resin of ethylene propylene; vinyl chloride; vinylidene chloride; vinyl fluoride; vinylidene fluoride; vinyl acetate; acrylonitrile; (metha)acrylic acid esters; a polymer and/or copolymer of styrene, butadiene or the like, polyamide resin; polyester resin; polyurethane resin; epoxy resin; phenolic resin or the like.

As an example, 100 parts of the resin are mixed preferably with 0.5–200 wt. parts of the organo-tin compound.

When the article having a water exposed surface is a melt-spun fibrous material, the latter must naturally be of a thermoplastic nature. In this case, 0.5–5 wt. parts of the organo-tin compound(s) may preferably be blended therewith.

When the anti-fouling substance is applied through the coating technique, the organo-tin compound in solution is preferably used. The cooperating resin may be an ethylene/vinyl acetate copolymer, including 15–40 wt.% vinyl acetate component and having a melt index, ASTM D-1238, of 2–400 g/10 min.

It may be polyvinyl chloride; vinylidene/vinyl chloride copolymer; polyamide resin; polyethylene; polypropylene; polyester; polyvinyl acetate; acrylonitrile/styrene/butadiene copolymer, or the like.

The solvent is preferably selected from the following group: acetoaldehyde; acetone; ethyl acetate; propyl acetate; benzene; toluene; xylene; cyclohexane; cyclohexene; tetrahydrofuran; heptane; hexane; kerosene;

solvent naphtha; gasoline; tetrachloroethylene; trichloroethylene or the like.

The organo-tin compound (1-20 wt.% and resin (2-20 wt.% may be dissolved or suspended in the solvent and applied to the article by any conventional coating method.

MANUFACTURING EXAMPLE 1

Manufacture of trimethyl-n-dodecyl tin

Grignard reagent comprising methyl iodide 1727.8 g and metallic magnesium 325.6 g was reacted in n-butyl ether equivolumetric to the methyl iodide, with a solution of n-dodecyl tin trichloride, 1280 g, in n-butyl ether at 30° C of reaction temperature, and conventionally after-treated. The formed organic phase was distilled to trimthyl-n-dodecyl tin, 761 g. Yield: 70.4% based upon the charged n-dodecyl tin trichloride.

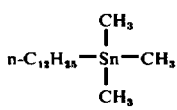

b.p. 110°–114° C/0.75 mmHg;
$n^{20}$ 1.4620.

MANUFACTURING EXAMPLE 2

Manufacture of bis-(dimethyl-n-dodecyl tin) oxide

Dimethyl-n-dodecyl tin iodide (compound in Example 5 to follow), 869 g, was dissolved in benzene, 6 lit., and added with a 10 wt.% caustic soda solution including caustic soda, 117 g., said mixture being subjected to hydrolysis at 30°–40° C.

Upon completion of the reaction, the benzene phase was separated and the benzene phase was distilled off. The solid residual was added to acetone and refined through recrystallization to bis-(dimethyl-n-dodecyl tin) oxide, 411.9 g.

Yield: 64.7% based upon the introduced dimethyl-n-dodecyl tin iodide.

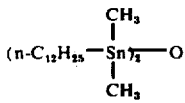

m.p. 40°–42° C;
State: white powder.

MANUFACTURING EXAMPLE 3

Manufacture of dimethyl-n-dodecyl tin stearate (see also Example 18)

Bis-(dimethyl-n-dodecyl tin) oxide, 374.1 g and stearic acid, 326.4 g, were added to toluene, 5.5 kg and brought into reaction for 3 hours under refluxing conditions. By observing a substantially theoretical amount of distilled water in a water separator attributed thereto, it was adjudged that the reaction had progressed substantially stoichiometrically.

Upon termination of the reaction, toluene was distilled off and the residual white solid product was found to be dimethyl-n-dodecyl tin stearate, 690 g.

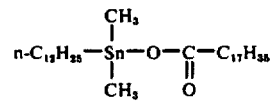

m.p. 50° C.

MANUFACTURING EXAMPLE 4

Manufacture of dimethyl-n-dodecyl tin-1-hydroxyethyl-2-undecyl-2-carboxymethyl-2-imidazolinium hydroxide (refer also to Example 45 to follow)

Dimethyl-n-dodecyl tin chloride, 35.4 g, and sodium-1-hydroxyethyl-2-undecyl-2-carboxymethyl-2-imidazolinium hydroxide, 36.7 g, were added to toluene, 150 ml, and the mixture was brought into reaction for 3 hours under refluxing conditions. The formed sodium chloride was filtered off. Toluene was distilled off from the organic phase and white yellow paste, 66 g. The separated sodium chloride weighed 5.5 g in its dried weight. The yield of the effective substance amounted to 94% upon consideration of the above.

In the following, the invention will be demonstrated more specifically by way of a number of Examples.

EXAMPLE 1

By the following several Examples, it is shown that the trialkyl tin compound containing different alkyls in accordance with the invention has a highly superior anti-fouling performance and co-kneading performance with synthetic resin over a conventional anti-fouling agent having the same trialkyl tin radicals of same.

The anti-fouling performance tests were carried out in the following way.

The compound under test was dissolved in benzene and the concentration was properly adjusted to remain uniform at 0.0003 mole of the compound per $cm^2$ by coating administration thereof with a painting brush on a smooth square plate (5 × 20 × 1 cm) prepared from a Japanese oak tree and thereupon dried. The thus coated plate was immersed in sea water to a depth of 1.5 m.

The co-kneadability in the above sense was measured in the following way.

A mass of polyethylene ("Sholex 6006C", manufactured and sold by a Japanese chemical firm, SHOWA DENKO KABUSHIKI KAISHA, Kawasaki, Japan) was admixed with the anti-fouling agent in ratios of 2 and 4 PHR, respectively, and compounded at 150° C for 3 minutes by calendering. During this mixing operation the co-miscibility of the anti-fouling agent and the kneadability of the compound were measured.

The bleedability of the anti-fouling agent on the surface of a polyethylene solid sheet by pressing the compound at 250° C for 10 or 20 minutes, respectively, was also observed. The bleedability was also observed visually upon lapse of a week at normal temperature on the same polyethylene solid sheet or panel. The bleedability as listed in the following was determined from a general consideration of these tests.

As references, tributyl tin and dimethyl-n-hexyl tin compounds were used. By use of these known compounds, irritating smells were plentiful in the working atmosphere when performing calendering and the like at elevated temperature. With use of the inventive anti-fouling agent of the trialkyl tin compound having at least a higher alkyl radical as proposed by the present invention, such defect was not encountered.

most unchanged anti-fouling capabilities even when the negative substituent radicals are replaced by other

TABLE 3

| | | | Total number of carbons | Physical Constants | | Anti-fouling performance | | Co-kneadability |
|---|---|---|---|---|---|---|---|---|
| | | | | Ref.index. $n^{25}$ | m.p. °C | After one month | After 3 months | |
| Compound in Example | bis-dimethyl-n-dodecyl tin)oxide $\left(\begin{array}{c} C_{12}H_{25} \\ CH_3-Sn \\ CH_3 \end{array}\right)_2 O$ | 1 | 14 | | 40–42 | 0 | 0 | Best |
| References | bis-(dimethyl-n-hexyl tin) oxide $\left(\begin{array}{c} C_6H_{13} \\ CH_3-Sn \\ CH_3 \end{array}\right)_2 O$ | 1 | 8 | 1.4855 | | 0 | Δ | Bad |
| | bis-(tri-n-butyl tin) oxide $\left(\begin{array}{c} C_4H_9 \\ C_4H_9-Sn \\ C_4H_9 \end{array}\right)_2 O$ | 2 | 12 | | | 0 | Δ | Bad |
| | bis-(diethyl-n-dodecyl tin) oxide $\left(\begin{array}{c} C_{12}H_{25} \\ C_2H_5-Sn \\ C_2H_5 \end{array}\right)_2 O$ | 3 | 14 | 1.4863 | | Δ | X | Good |
| | bis-(dimethyl-n-tetradecyl tin) oxide $\left(\begin{array}{c} C_{14}H_{29} \\ CH_3-Sn \\ CH_3 \end{array}\right)_2 O$ | 4 | 16 | 1.4840 | | Δ | X | Good |

Remarks: Degree of fouling is expressed as follows:
0: practically no deposition of water micro-organisms
Δ: small quantity of deposited water micro-organisms observed
X: overall and substantial deposition observed.

EXAMPLES 2–8

By these examples, it is shown that the trialkyl tin compounds having different kinds of alkyls show almost unchanged anti-fouling capabilities even when the negative substituent radicals are replaced by other radicals. Even if the capabilities should be changed, this is only slightly caused by the altered physical constants.

The fouling tests were executed as before.

TABLE 4

| | | Molecular structure of organo-tin compound or anti-fouling agent according to this invention | | Physical Constants | | Anti-Fouling Performance | |
|---|---|---|---|---|---|---|---|
| | Test No. | Trialkyl-tin radical | Negative substitute radical | Ref.Index $n^{25}$ | m.p. °C | 1 month | 3 months |
| Compounds Examples | 2 | n-C$_{12}$H$_{25}$\\ CH$_3$—Sn—X / CH$_3$ | Cl | | 26.5 | 0 | Δ |
| | 3 | | OC$_2$H$_5$ | 1.4700 | | 0 | Δ |
| | 4 | | OC$_2$H$_4$OC$_4$H$_9$ | 1.4702 | | 0 | 0 |
| | 5 | | OC$_{12}$H$_{25}$ | 1.4660 | | 0 | 0 |
| | 6 | | O . CO . CH$_3$ | | 99–102 | 0 | Δ |
| | 7 | | O . CO . C$_{17}$H$_{35}$ | | 50 | 0 | 0 |
| | 8 | | S . C$_{12}$H$_{25}$ | 1.4839 | | 0 | 0 |
| References | 5 | n-C$_6$H$_{13}$\\ CH$_3$—Sn—X / CH$_3$ | Cl | | | 0 | X |
| | 6 | | OC$_2$H$_5$ | 1.4755 | | 0 | X |
| | 7 | | OC$_2$H$_4$OC$_4$H$_9$ | 1.4688 | | 0 | X |
| | 8 | | OC$_{12}$H$_{25}$ | 1.4660 | | 0 | Δ |
| | 9 | | O . CO . CH$_3$ | | 81–82 | 0 | X |
| | 10 | | O . CO . C$_{17}$H$_{35}$ | 1.4769 | | 0 | Δ |
| | 11 | | S . C$_{12}$H$_{25}$ | 1.4902 | | 0 | Δ |

TABLE 4-continued

| Test No. | Molecular structure of organo-tin compound or anti-fouling agent according to this invention | | Physical Constants | | Anti-Fouling Performance | |
|---|---|---|---|---|---|---|
| | Trialkyl-tin radical | Negative substitute radical | Ref.Index $n^{25}$ | m.p. °C | 1 month | 3 months |
| 12 | n-$C_4H_9$\\Sn—X/n-$C_4H_9$ | Cl | 1,4890 | | 0 | X |
| 13 | | O . CO . $CH_3$ | | 77–79 | 0 | X |
| 14 | n-$C_4H_9$ | O . CO . $C_{17}H_{35}$ | | 37 | 0 | Δ |
| 15 | | Cl | | 26 | 0 | Δ |
| 16 | n-$C_{12}H_{25}$\\Sn—X/$C_2H_5$ | O . $C_2H_5$ | 1,4757 | | Δ | X |
| 17 | | $OC_2H_4$ . $OC_4H_9$ | 1,4728 | | Δ | X |
| 18 | $C_2H_5$—Sn—X | $OC_{12}H_{25}$ | 1,4710 | | Δ | X |
| 19 | | O . CO . $CH_3$ | | 68–72 | Δ | X |
| 20 | $C_2H_5$ | O . CO . $C_{17}H_{35}$ | | 34–36 | Δ | X |
| 21 | | S . $C_{12}H_{25}$ | 1,4873 | | 0 | Δ |

EXAMPLE 9

In this Example, polyethylene fishing nets were coated with an anti-fouling composition comprising the organo-tin compound as the effective substance according to this invention and a base material consisting of ethylene/vinyl acetate copolymer. As the fishing nets, those made of vinylidene chloride/vinyl chloride copolymer (Krehalon, manufactured and sold by Kureha Chemical Industrial Co., Ltd., Tokyo, Japan), were also tested. At the same time, effects of spreaders usable in the invention are also shown.

In the following Table 5, a preferred anti-fouling composition is shown. Table 6, the characteristic of this composition is shown. In Table 7, the anti-fouling effects of the fishing nets (per 1 m × 1 m) are shown.

TABLE 5

| No. of Example | Preferred Composition | |
|---|---|---|
| | Constituents | wt. parts |
| 9 | dimethyl-n-dodecyl tin stearate (m.p., 50° C); | 3 |
| | ethylene (75 wt.%)/vinyl acetate (25 wt.%) copolymer (melt index 150); | 5 |
| | solvent naphtha | 92 |
| Ref. 22 | methacrylate (60 wt.%)/tributyl tin acrylate (40 wt.%) copolymer; | 10 |
| | solvent naphtha; | 90 |
| Ref. 23 | bis-(tri-n-butyl tin) oxide; | 50 |
| | copper naphthenate (containing 10 wt.% of copper) | 30 |
| | solvent naphtha; | 65 |
| Ref. 24 | tri-n-butyl tin naphthenate; | 5 |
| | copper naphthenate (containing 10 wt.% of copper) | 5 |
| | oil varnish | 90 |

TABLE 6

| | | Polyethylene Nets | | |
|---|---|---|---|---|
| | | Adhesion* | Blocking | Surface Concentration of Organo-tin** |
| Preferred example of the invention | 9 | no scale-off | non-sticky | 6.5 times |
| References | 22 | bad | somewhat sticky | 1.3 times |
| | 23 | bad | non-sticky | 1.5 times |
| | 24 | bad | somewhat sticky | 1.2 times |
| | | "Krehalon" Nets | | |
| | | Adhesion* | Blocking | Surface Conentration of Organo-tin** |
| Preferred examples of the invention | 9 | no scale-off | non-sticky | 6.3 times |
| References | 22 | unfavorable | somewhat sticky | 1.3 times |
| | 23 | bad | non-sticky | 1.4 times |
| | 24 | bad | somewhat sticky | 1.3 times |

Remarks:
*Fishing net was coated with anti-fouling agent, dried under moving atmosphere at room temperature for 24 hours, stuck with an adhesive tape, peeled off and the adhesive conditions of the peeled-off surface of the net for inspection of the adhesive conditions thereof.
**Ratio of surface concentration (organo-tin/developer) upon coating and drying/to the concentration of anti-fouling agent solution (concentration of organo-tin/developer).

TABLE 7

Results of Anti-Fouling Tests

| Material | | Degree of Deposition of Water Micro-Organisms* after Immersion of testing Materials into the Sea | | |
|---|---|---|---|---|
| | | After 2 months | After 4 months | After 6 months |
| Preferred Example of the Invention | 9 | 0 | 0 | 0** |
| References | 22 | 0 | Δ | X |
| | 23 | 0 | Δ | X |

TABLE 7-continued

Results of Anti-Fouling Tests

| Material | Degree of Deposition of Water Micro-Organisms* after Immersion of testing Materials into the Sea | | |
|---|---|---|---|
| | After 2 months | After 4 months | After 6 months |
| 24 | 0 | Δ | X |

Remarks:
*"Water micro-organisms" comprise shellfishes such as barnacle, serpula, polyzona, mussel, ascidian and the like, and algae such as laver, green laver and the like.
**0: almost no deposition of water micro-organisms observed;
Δ: small quantity of deposited water micro-organisms observed;
X: overall and substantial deposition observed.

EXAMPLES 10–26

In these Examples, fishing nets and ropes made of polyethylene blended with the organo-tin anti-fouling agent according to this invention were tested.

In these tests, the organo-tin anti-fouling agent was added to pulverized polyethylene ("Sholex-6006C") and dry-blended intimately and the thus compounded mass was spun into filaments, 400 denier, by the melt-spinning process. The spinning unit was of the double pitch type fitted with a screw, 60 mm diameter. L/D = 22; compression rate — 3.0. The orifice plate was formed with 79 extrusion orifices, each being of 2 mm diameter. The stretch ratio was 10:1, extrusion rate: 300 g/min; internal temperature, mx., 275° C. The amount of the compound consumed per batch: 59 kg.

The physical properties such as tensile strength, elongation and knot strength of the filaments when spun from a blended spinning material with the organo-tin anti-fouling agent in the form of tributyl-tin compound showed somewhat lesser values.

Further, it should be noted that when the blended spinning material with tributyl-tin compound was spun, an unpleasant and irritating smell resulted. Since tributyl-tin is a highly poisonous substance, the spinning job must be carried out by the hands of operating personnel provided with completely sealed working clothes, resulting in almost impracticability of spinning. On the other hand, with use of the novel organo-tin compounds, the spinning job could be performed with no difficulty.

The aforementioned difficulty by use of tributyl-tin compound or the like can be attributed to the higher vapor pressure of the trialkyl-tin compound than the former.

The filaments blended with the various organo-tin anti-fouling agents were fabricated into ropes, each having a 12 mm O.D., which were then immersed into sea water to test the anti-fouling effect against sea micro-organisms. The results thereof, together with the respective compositions of the blended materials with the organo-tin compounds are shown in the following Table 8.

TABLE 8

Specification of Mixed Compound

| | | Organic-tin anti-fouling agent | | Ionol** | DLTDP*** | Anti-fouling**** reference | |
|---|---|---|---|---|---|---|---|
| | | Chemical Compound and Physical Data O | (PHR)* | (PHR) | (PHR) | after 2 months | after 6 months |
| Compound Examples | 10 | $\left[\begin{array}{c} n\text{-}C_{12}H_{25} \\ CH_3-Sn \\ CH_3 \end{array}\right]_2$ O  (m.p. 40–42° C)***** | 0.5 | — | — | 0 | 0 |
| | 11 | | 2.0 | — | — | 0 | 0 |
| | 12 | | 2.0 | 0.1 | 0.1 | 0 | 0 |
| | 13 | | 4.0 | — | — | 0 | 0 |
| | 14 | n-C$_{12}$H$_{25}$\\CH$_3$—Sn—O—C—C$_{17}$H$_{35}$ / ‖ CH$_3$  O  (m.p. 50° C) | 0.5 | 0.1 | 0.1 | 0 | 0 |
| | 15 | | 1.0 | 0.1 | 0.1 | 0 | 0 |
| | 16 | | 3.0 | 0.1 | 0.1 | 0 | 0 |
| | 17 | n-C$_{12}$H$_{25}$\\CH$_3$—Sn—O—C—CH$_3$ / ‖ CH$_3$  O  (m.p. 99–102° C) | 1.0 | 0.1 | 0.1 | 0 | Δ |
| | 18 | n-C$_{12}$H$_{25}$\\CH$_3$—Sn—O—C$_{12}$H$_{25}$ / CH$_3$  ($n^{25}$ = 1.4710) | 1.0 | 0.1 | 0.1 | 0 | 0 |
| | 19 | n-C$_{12}$H$_{25}$\\CH$_3$—Sn—(OCH$_2$CH$_2$)$_{30}$—O—C$_{12}$H$_{25}$ / CH$_3$  ($n^{25}$ = 1.4609) | 2.0 | 0.1 | 0.1 | 0 | Δ |
| | 20 | | 3.0 | 0.1 | 0.1 | 0 | 0 |
| | 21 | | 4.0 | 0.1 | 0.1 | 0 | 0 |
| | 22 | n-C$_{12}$H$_{25}$\\CH$_3$—Sn—(OCH$_2$CH$_2$)$_{30}$—O—⟨C$_6$H$_4$⟩—C$_9$H$_{19}$ / CH$_3$  ($n^{25}$ = 1.4851) | 3.0 | 0.1 | 0.1 | 0 | 0 |
| | 23 | n-C$_{12}$H$_{25}$\\CH$_3$—Sn—(OCH$_2$CH$_2$)$_{15}$—O—C—C$_{17}$H$_{35}$ / ‖ CH$_3$  O  (m.p. 30–36.5° C) | 2.0 | 0.1 | 0.1 | 0 | Δ |
| | 24 | | 4.0 | 0.1 | 0.1 | 0 | 0 |

TABLE 8-continued

| | Specification of Mixed Compound | | | | Anti-fouling**** reference | |
|---|---|---|---|---|---|---|
| | Organic-tin anti-fouling agent | | Ionol** | DLTDP*** | after | after |
| | Chemical Compound and Physical Data O | (PHR)* | (PHR) | (PHR) | 2 months | 6 months |
| 25 | n-C₁₂H₂₅\CH₃—Sn—N—C₁₂H₂₅ /CH₃  H   (n²⁵ = 1.4690) | 3.0 | 0.1 | 0.1 | 0 | 0 |
| 26 | (complex organo-tin structure, n²⁵ = 1.4835) | 2.0 | 0.1 | 0.1 | 0 | 0 |
| References 25 | (n-C₄H₉)₃Sn—O (n²⁰ = 1.4872) | 4.0 | 0.1 | 0.1 | X | — |
| 26 | | 4.0 | — | — | X | — |
| 27 | n-C₄H₉\ n-C₄H₉—Sn—O—C—C₁₇H₃₅ / n-C₄H₉  ‖ O  (m.p. 37° C) | 1.0 | 0.1 | 0.1 | X | — |
| 28 | | 3.0 | 0.1 | 0.1 | Δ | X |
| 29 | n-C₄H₉\ n-C₄H₉—Sn—(OCH₂CH₂)₂₀—O—C₁₂H₂₅ / n-C₄H₉  (m.p. 28–30° C) | 2.0 | 0.1 | 0.1 | X | — |
| 30 | | 4.0 | 0.1 | 0.1 | X | — |

Remarks:

*added weight quantity to 100 weight parts of resin.

**DEP: diethylphthalate.

***alpha-MBE, di-alpha-methylbenzylether.

****0: almost no deposition of water micro-organisms observed.

Δ: small quantity of deposited water micro-organisms observed.

X: overall and substantial deposition observed.

*****The numerical data set forth as recited above represented either refractive index or melting point, as the case may be.

EXAMPLE 27

In these tests, fishing nets made of vinylidene chloride blended beforehand with the organo-tin compound according to this invention were examined.

The organo-tin anti-fouling agent, together with a proper additive, was added to vinylidene chloride/vinyl chloride copolymer Krehalon resin, manufactured and sold by Kureha Chemical Industrial Co., Ltd., Tokyo, and blended together according to the conventional blending technique. In this way, several batches of compounded masses, each amounting to 50 kg, were prepared. These blended materials were melt-spun, under conventionally employed spinning conditions, into filaments of 1,000 denier. The blending of the organo-tin compound did not adversely affect the desirous physical properties of the filaments as spun, such as tensile strength, elongation, knot strength and loop strength. The bleeding characteristics of the anti-fouling agent towards the surfaces of the filaments or ropes made therefrom were not adversely affected.

The yarns or ropes made from these filaments were then fabricated into fishing nets which were then immersed into the sea, 1–3 m deep, for testing of the anti-fouling effect. The results of these tests and the specifications of the compounded materials are given in the following Table 9.

TABLE 9

Specification of Mixed Compound

| | | Organo-tin anti-fouling agent Chemical Compound and Physical Data | (PHR)* | DEP** (PHR) | alpha-*** MBE (PHR) | barium stearate (PHR) | carbon black (PHR) | Anti-Fouling Performance**** after 2 months | after 6 months |
|---|---|---|---|---|---|---|---|---|---|
| Compound Examples | 28 | n-C$_{12}$H$_{25}$\Sn—O—C—C$_{17}$H$_{35}$ / CH$_3$ ‖ O  (m.p. 50° C) | 1.0 | 2 | 3 | 0.5 | 0.065 | O | O |
| | 29 | | 1.8 | 2 | 3 | 0.5 | — | O | O |
| | 30 | | 3.0 | 2 | 3 | 0.5 | 0.065 | O | O |
| | 31 | | 3.0 | 2 | 3 | 0.5 | — | O | O |
| | 32 | n-C$_{12}$H$_{25}$\Sn—(OCH$_2$CH$_2$)$_{7.5}$O—⟨ ⟩—C$_4$H$_{19}$ / CH$_3$   (n$^{25}$=1.4851) | 1.0 | 2 | 3 | 0.5 | 0.065 | O | Δ |
| | 33 | | 2.0 | 2 | 3 | 0.5 | 0.065 | O | O |
| | 34 | | 3.0 | 2 | 3 | 0.5 | 0.065 | O | O |
| | 35 | n-C$_{12}$H$_{25}$\Sn—(OCH$_2$CH$_2$)$_{7.5}$O—C—C$_{17}$H$_{35}$ / CH$_3$ ‖ O  (m.p. 30–36.5° C) | 3.0 | 2 | 3 | 0.5 | 0.065 | O | O |
| References | 25 | n-C$_4$H$_9$\Sn—O—C—C$_{17}$H$_{35}$ / n-C$_4$H$_9$ ‖ O  (m.p. 37° C) | 1.0 | 2 | 3 | 0.5 | 0.065 | X | — |
| | 26 | | 2.0 | 2 | 3 | 0.5 | 0.065 | Δ | X |
| | 27 | | 3.0 | 2 | 3 | 0.5 | 0.065 | Δ | X |
| | 28 | n-C$_4$H$_9$\Sn—(OCH$_2$CH$_2$)$_{7.5}$O—C—C$_{17}$H$_{35}$ / n-C$_4$H$_9$ ‖ O  (m.p. 37° C) | 2.0 | 2 | 3 | 0.5 | 0.065 | X | — |
| | 29 | | 3.0 | 2 | 3 | 0.5 | 0.065 | X | — |

Remarks:
*added weight quantity to 100 weight parts of resin.
**DEP; diethylphthalate;
***alpha-MBE, di-alpha-methylbenzylether.
****O: almost no deposition of water micro-organisms observed.
Δ: small quantity of deposited water micro-organisms observed.
X: overall and substantial deposition observed.

What is claimed is:

1. An article to be used on or in the water, at least the surfaces of said article comprising an anti-fouling composition comprising a synthetic resin and an amount of a substance effective to prevent fouling which comprises 0.5–200 parts by weight based on 100 parts by weight of said synthetic resin of an organo-tin compound of the formula:

$$R_1-\underset{\underset{R_3}{|}}{\overset{\overset{R_2}{|}}{Sn}}-X$$

wherein $R_1$ is n-dodecyl, $R_2$ and $R_3$ are methyl and X stands for a.

$$R_4-\underset{\underset{R_6}{|}}{\overset{\overset{R_5}{|}}{Sn}}-O$$

wherein $R_4$ is a $C_8$–$C_{12}$ alkyl group and $R_5$ and $R_6$ are $C_1$–$C_3$ alkyl groups, the total number of alkyl carbon atoms in $R_4$, $R_5$ and $R_6$ being less than 15;

b. halogen;

c. an alkoxyl radical selected from the group consisting of a residue of a saturated or unsaturated straight chain or branched aliphatic alcohol, a saturated or unsaturated cycloaliphatic alcohol and an aromatic alcohol, the number of carbon atoms being 3–24, d. a thioalkoxyl radical selected from the group consisting of a residue of a saturated or unsaturated straight chain or branched aliphatic thioalcohol, a saturated or unsaturated cycloaliphatic thioalcohol and an aromatic thioalcohol, the number of carbons included in the alcohol being 3–24; or e. an organic acid radical selected from the group consisting of a mono-, di- or tribasic $C_2$–$C_{24}$ saturated, unsaturated, straight chain or branched chain aliphatic, cycloaliphatic and aromatic carboxylic acid.

2. The article of claim 1, wherein if X is halogen X is a member selected from the group consisting of bromine, chlorine and iodine.

3. The article of claim 1 wherein said synthetic resin is selected from the group consisting of ethylene resin, propylene resin, vinyl chloride resin, vinylindene chloride resin, vinyl fluoride resin, vinylindene fluoride resin, vinyl acetate resin, acrylonitrile resin, (metha)acrylic acid ester resins, styrene polymer or copolymer resins, butadiene polymer or copolymer resins, polyamide resins, polyester resins, polyurethane resins, epoxy resins and phenolic resins.

* * * * *